(12) United States Patent
Bhushan et al.

(10) Patent No.: US 10,561,614 B2
(45) Date of Patent: Feb. 18, 2020

(54) TENOFOVIR GRANULES

(71) Applicant: STEERLIFE INDIA PRIVATE LIMITED, Bengaluru, Karnataka (IN)

(72) Inventors: Indu Bhushan, Karnataka (IN); Vinay Rao, Karnataka (IN); Radhika Ghike, Karnataka (IN)

(73) Assignee: STEERLIFE INDIA PRIVATE LIMITED, Bengaluru, Karnataka (IN)

( * ) Notice: Subject to any disclaimer, the term of this patent is extended or adjusted under 35 U.S.C. 154(b) by 0 days.

(21) Appl. No.: 15/881,413

(22) Filed: Jan. 26, 2018

(65) Prior Publication Data

US 2018/0214378 A1 Aug. 2, 2018

(30) Foreign Application Priority Data

Jan. 27, 2017 (IN) .............................. 201741003161

(51) Int. Cl.
| | |
|---|---|
| *A61K 9/16* | (2006.01) |
| *A61K 31/675* | (2006.01) |
| *A61K 9/20* | (2006.01) |
| *A61K 31/683* | (2006.01) |
| *A61P 1/16* | (2006.01) |

(52) U.S. Cl.
CPC .......... *A61K 9/1688* (2013.01); *A61K 9/2009* (2013.01); *A61K 9/2013* (2013.01); *A61K 9/2054* (2013.01); *A61K 31/675* (2013.01); *A61K 31/683* (2013.01)

(58) Field of Classification Search
None
See application file for complete search history.

(56) References Cited

U.S. PATENT DOCUMENTS

| | | | | |
|---|---|---|---|---|
| 2011/0112292 A1* | 5/2011 | Phull | ................... | C07F 9/65616 544/244 |
| 2011/0288045 A1* | 11/2011 | Ramos | ................. | A61K 9/1652 514/49 |
| 2013/0243857 A1* | 9/2013 | Oliyai | .................... | A61K 9/209 424/465 |

FOREIGN PATENT DOCUMENTS

| | | | | |
|---|---|---|---|---|
| CN | 103330683 | | 12/2014 | |
| EP | 1890681 B1 | | 1/2009 | |
| EP | 2389929 A1 | | 11/2011 | |
| IN | 843/CHE/2013 | | 10/2014 | |
| IN | 2621/CHE/2013 | | 12/2014 | |
| WO | WO-2015163724 A1 * | | 10/2015 | ............. A61K 31/52 |

OTHER PUBLICATIONS

WO-2015163724-A1 Google translation, pp. 1-6. 2015 (Year: 2015).*
Manikandan et al., "Formulation development and evaluation of Emtricitabine and Tenofovir Disproxil Fumarate Tablets," International Journal of Drug Development & Research, vol. 4, Issue 1, pp. 247-256 (Jan.-Mar. 2012).

* cited by examiner

*Primary Examiner* — Kyung S Chang
(74) *Attorney, Agent, or Firm* — Merchant & Gould P.C.

(57) ABSTRACT

The present invention relates to a granular composition comprising essentially Tenofovir, wherein the composition is devoid of an excipient. Tenofovir granules of the present invention are prepared in twin-screw processor such that the content of total impurities in the prepared granules is less than 2.0%.

9 Claims, 2 Drawing Sheets

TENOFOVIR GRANULES

This application claims benefit of Serial No. 201741003161, filed 27 Jan. 2017 in India and is incorporated herein by reference. To the extent appropriate, a claim of priority is made to the above disclosed application.

FIELD OF THE INVENTION

The present invention relates to a granular composition consisting essentially of Tenofovir, wherein the composition is devoid of an excipient.

BACKGROUND OF THE INVENTION

Tenofovir, is chemically, 9-[2-(R)-(phosphonomethoxy)propyl]adenine (PMPA). Tenofovir disoproxil is a pro-drug of Tenofovir. It has increased oral bioavailability compared to Tenofovir. Tenofovir is approved for commercial use as in the form of Tenofovir disoproxil fumarate (TDF), chemically known as 9-[(R)-2-[[bis[[(isopropoxycarbonyl)oxy]methoxy]phosphinyl]methoxy]propyl]adenine fumarate (1:1).

Tenofovir Disoproxil Fumarate 300 mg Tablets are indicated in combination with other anti-retrovirals for the treatment of HIV-1 infection in adults and adolescents aged over 12 years. Tenofovir Disoproxil Fumarate 300 mg Tablets are indicated for the treatment of chronic hepatitis B in adults and adolescents aged over 12 years with compensated liver disease, with evidence of active viral replication, persistently elevated serum alanine aminotransferase (ALT) levels and histological evidence of active inflammation and/or fibrosis.

Tenofovir disoproxil fumarate (TDF) is observed to have poor flow properties, therefore aqueous or non-aqueous wet granulation is a preferred processing step in the formulation of the TDF tablets, by most pharmaceutical manufacturers. Also, as per International Journal of Drug Development & Research, 2012, Volume 4, Issue 1, Pages 247-256; for Emtricitabine and Tenofovir disoproxil fumarate film coated tablets, wet granulation with pregelatinized starch as binder was found to be the best method of choice for formulation of these tablets, as compared to direct compression.

Literature is also available on non-wet granulation techniques for compounding Tenofovir. For example—EP 2389929A1 discloses compositions of Tenofovir with pregelatinized starch (5-15%) by weight prepared by direct compression. IN 2621/CHE/2013 discloses a hot-melt extruded Tenofovir disoproxil composition having a binder. 843/CHE/2013 discloses an extrusion-spheronization process for preparation of oral multi-particulate compositions composed of Tenofovir coated with ethyl cellulose or methacrylic acid co-polymers. CN103330683 B discloses hot-melt extrusion of Tenofovir disoproxil fumarate with sweetener and polymer Kollidon® VA64, Kollicoat® IR and Soluplus® to prepare fine granules. European Patent Document EP1890681 B1 describes a method comprising dry granulating a composition comprising a pharmaceutically acceptable excipient, emtricitabine and tenofovir DF to produce dry granules.

However, none of the references suggest or disclose free flowing directly compressible Tenofovir granules devoid of an excipient, or a process for preparation of such granules. Such granules would be specifically more advantageous in case of unit dose antiretroviral oral fixed dose combinations where there is a larger percentage of API in the finished dosage form. For example—Atripla® tablets, Complera® tablets, Stribild® tablets, Emtricitabine 200 mg/Tenofovir disoproxil fumarate 300 mg+Nevirapine 200 mg tablets, etc. Besides, since TDF is sensitive towards hydrolytic degradation. It would be highly desirable to process TDF in conditions which can prevent or minimize such hydrolytic degradation. Further, it would be most desirable to prepare free flowing directly compressible Tenofovir granules devoid of an excipient which can remain stable at 40° C. and 75% relative humidity for three months.

As per, Authorized USP Pending Monograph Version 1; following are the impurities known for Tenofovir Disoproxil Fumarate—

Tenofovir isoproxil monoester—({[(R)-1-(6-Amino-9H-purin-9-yl) propan-2-yloxy]methyl}(hydroxy)phosphoryloxy)methyl isopropyl carbonate Tenofovir isopropyl isoproxil—O-(Isopropoxycarbonyloxymethyl)-O-isopropyl-{(R)-[1-(6-amino-9H-purin-9-yl) propan-2-yloxy]}methylphosphonate Tenofovir disoproxil ethyl ester—O-(Ethoxycarbonyloxymethyl)-O-(isopropoxycarbonyloxymethyl)-{(R)-[1-(6-amino-9H-purin-9-yl) propan-2-yloxy]}methylphosphonate Tenofovir disoproxil carbamate—O,O-Bis(isopropoxycarbonyl oxymethyl){(R)-1-[(6-isopropoxycarbonylamino)-9H-purin-9yl]propan-2-yloxy]}methylphosphonate and Tenofovir disoproxil dimer—Tetra(isopropoxycarbonyloxymethyl) (2S)-1,1'-[6,6'-methylenebis(azanediyl)bis(9H-purine-9,6-diyl)bis(propane-2,1-diyl)bis(oxy)bis(methylene)diphosphonate.

In view of increasing demand for Tenofovir products, sources of quality-assured Tenofovir are constantly needed for the production of good-quality finished dosage forms. Also, TDF API (Active Pharmaceutical Ingredient) or dosage forms, with tighter specifications for impurities would be highly desirable.

OBJECTS OF THE INVENTION

It is an object of the invention to provide a granular composition consisting essentially of Tenofovir, wherein the composition is devoid of an excipient.

It is an object of the invention to provide a granular composition consisting essentially of Tenofovir, wherein the total impurities are not more than 2.0%.

It is another object of the invention to provide a process for preparation of a granular composition consisting of Tenofovir, devoid of an excipient, using a twin-screw processor.

It is another object of the invention to provide a tablet comprising i) the granular composition of Tenofovir prepared in twin screw processor having a content of total impurities of not more than 2.0% and ii) one or more pharmaceutically acceptable excipients.

SUMMARY OF THE INVENTION

According to an aspect of the present invention, there is provided a process for preparing a granular composition of Tenofovir in a twin screw processor comprising the steps of
a. feeding Tenofovir into the intake zone of the twin screw processor;
b. conveying Tenofovir towards the kneading zone and processing it in the kneading zone;
c. conveying Tenofovir from the kneading zone towards the exit;
d. collecting the Tenofovir granules; and wherein the temperature of the barrel is between 25° C. and 60° C., wherein the granules are devoid of an excipient.

According to another aspect of the present invention, there is provided a granular composition consisting essentially of Tenofovir, wherein the composition is devoid of an excipient and the content of total impurities is not more than 2.0%.

According to yet another aspect of the present invention there is provided a tablet comprising a) the granular composition of Tenofovir prepared in a twin screw processor having a content of total impurities of not more than 2.0% and b) one or more pharmaceutically acceptable excipients.

DETAILED DESCRIPTION OF THE INVENTION

Figure 1:
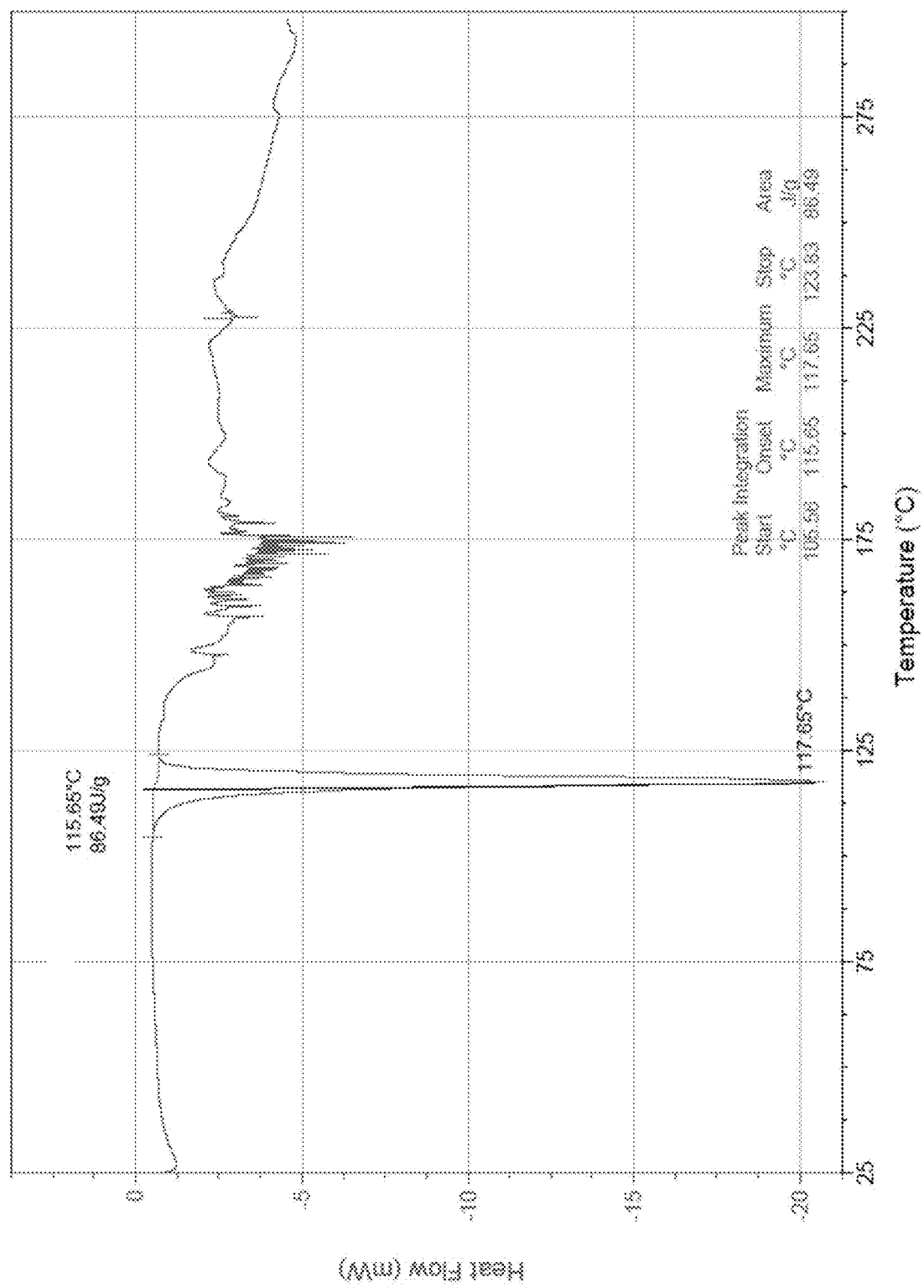
FIG. 1: DSC thermogram for TDF granules as per Example 5.
Figure 2:
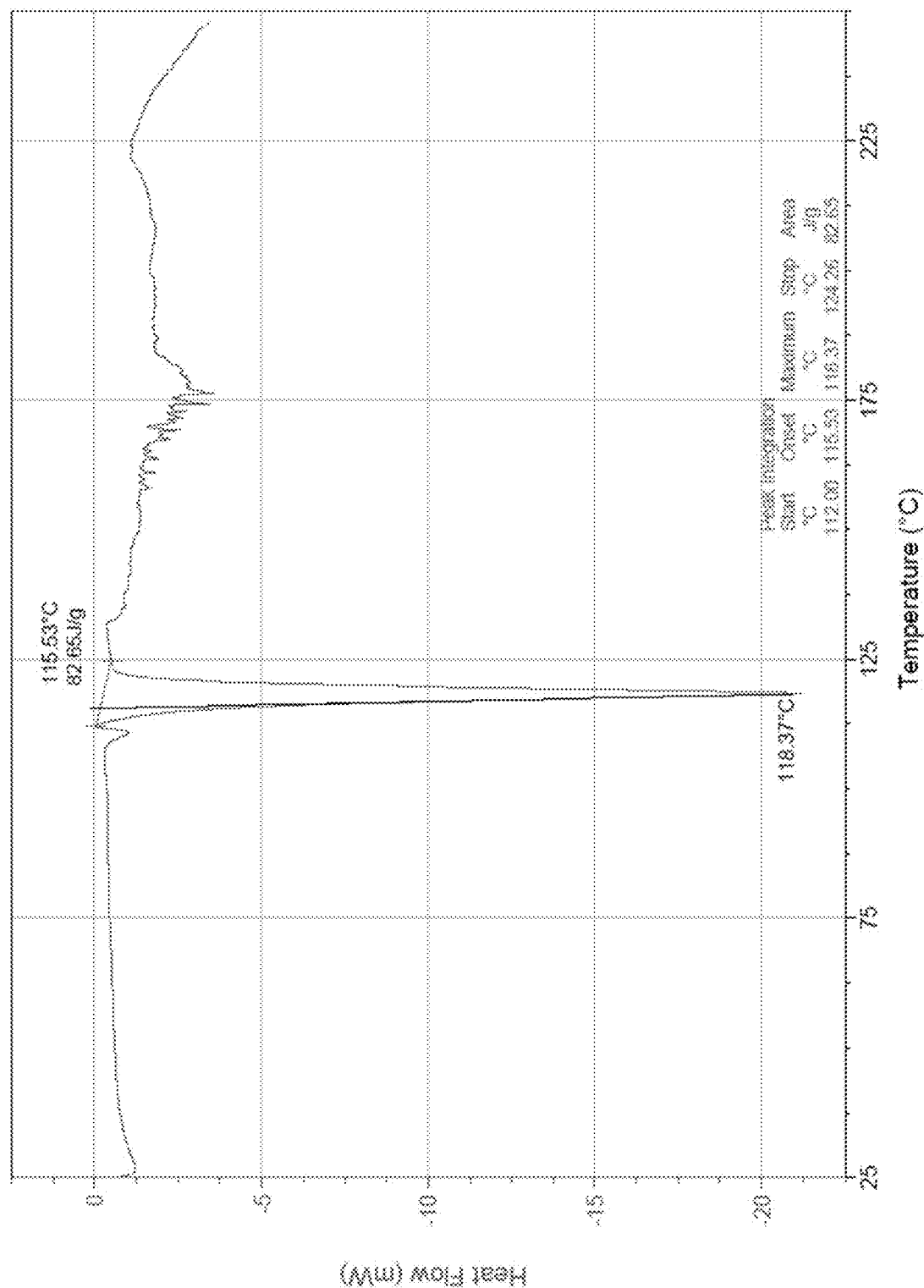
FIG. 2: DSC of TDF API before feeding into twin screw processor.

The present invention relates to a process for preparing a granular composition consisting essentially of Tenofovir, wherein the composition is devoid of an excipient.

Unless otherwise mentioned, the term "Tenofovir" as used herein, includes Tenofovir and pharmaceutically acceptable salts, esters, prodrugs or derivatives; or salts of said esters or prodrugs or derivatives, thereof. Tenofovir disoproxil fumarate is the preferred salt, which is the reason for describing the invention with reference to Tenofovir disoproxil fumarate, although it must not be considered to be limited only to the use of Tenofovir disoproxil fumarate.

The term "excipient" as used herein means substances used to formulate Tenofovir into pharmaceutical compositions. It also includes diluents, disintegrants, solubilizers, stabilizers, surfactants, binders, polymers, flow promoters, granulation aids and lubricants.

Unless otherwise mentioned, the term "consisting of" when used in connection with tenofovir means tenofovir inclusive of the known and unknown impurities as described in this specification.

In accordance with an embodiment, the present invention provides a granular composition consisting essentially of Tenofovir, wherein the composition is devoid of an excipient.

Such a composition can be directly compressed after mixing with one or more, pharmaceutically acceptable excipients, and is suitable for preparation of oral solid dosage forms, such as tablets. An excipient such as pregelatinized starch is not required as a pharmaceutically acceptable excipient for direct compression. The granular Tenofovir composition devoid of an excipient, itself has good compressibility and flow properties. Particularly, no additional excipients are required to prepare Tenofovir granules. This has more significance, in case of fixed dose combinations of Tenofovir with other anti-retrovirals, as unit dosage forms, wherein it can aid reduction in size of the unit dosage form. Some of the examples of other anti-retroviral active moieties or their pharmaceutically acceptable derivatives/analogues or other active pharmaceutical ingredient/s, that can be incorporated into such a fixed dose combination with Tenofovir are—Efavirenz, Emtricitabine, Rilpivirine, Lamivudine, Nevirapine, Elvitegravir, Dolutegravir and Cobicistat.

In accordance with a further embodiment, the granular Tenofovir composition devoid of an excipient, has a compressibility index of less than 30.

In accordance with an embodiment, the granular composition consisting essentially of Tenofovir can be prepared by twin screw granulation. Twin screw granulation refers to the process of granulation carried out in a twin-screw processor.

In accordance with an embodiment, the present invention provides a process for preparation of a granular composition consisting of Tenofovir, devoid of an excipient, using a twin-screw processor.

A co-rotating twin screw processor is used in one of the embodiments, to prepare the said granular composition of Tenofovir. The co-rotating twin-screw processor has two co-rotating screws inside a processor barrel. The processor barrel has barrel sections which are provided with temperature control means. These screws are open length wise, and closed cross wise. The co-rotating twin screw processor has a modular design for barrels and screws. Segmented screws convey and shear the materials in channels bound by screw flights and barrel walls, with short mass transfer distances. Each individual screw section is designed to perform specific functions such as conveying, mixing, shearing, or pressure building, thus allowing precise control of conditions along the screw length. The screw elements differ in pitch, pitch direction, length, and angle of offset. Pitch, length, and location of such screw elements on the shaft define a screw profile that influences the product characteristics. Due to variable screw configuration, the twin screw processor provides greater flexibility of operations to control characteristics of product by monitoring and regulating residence time, product temperature, pressure, and shear.

Alternatively, suitable extruders can also be used without a die at the exit. The barrel temperatures would depend on the kind of extruder or the kind of screw configuration within the extruder that is used.

During twin screw granulation process of Tenofovir disoproxil fumarate, in the co-rotating twin screw processor, the barrel temperature/s, screw speed and feed rate are adjusted such, that the following impurities or related substances known for Tenofovir disoproxil fumarate, viz.—

Tenofovir isoproxil monoester—({[(R)-1-(6-Amino-9H-purin-9-yl) propan-2-yloxy]methyl}(hydroxy)phosphoryloxy)methyl isopropyl carbonate, Tenofovir isopropyl isoproxil—O-(Isopropoxycarbonyloxymethyl)-O-isopropyl-{(R)-[1-(6-amino-9H-purin-9-yl) propan-2-yloxy]}methylphosphonate, Tenofovir disoproxil ethyl ester—O-(Ethoxycarbonyloxymethyl)-O-(isopropoxycarbonyloxymethyl)-{(R)-[1-(6-amino-9H-purin-9-yl) propan-2-yloxy]}methylphosphonate, Tenofovir disoproxil carbamate—O,O-Bis(isopropoxycarbonyl oxymethyl){(R)-1-[(6-isopropoxycarbonylamino)-9H-purin-9yl]propan-2-yloxy]}methylphosphonate, and Tenofovir disoproxil dimer—Tetra(isopropoxycarbonyloxymethyl) (2S)-1,1'-[6,6'-methylenebis(azanediyl)bis(9H-purine-9,6-diyl)]bis(propane-2,1-diyl)bis(oxy)bis(methylene)diphosphonate, are not increased, or increase minimally, after granulating TDF through the twin screw processor.

Such a process is simple and involves feeding of TDF into the co-rotating twin screw processor and collection of free flowing directly compressible (DC) TDF granules. The TDF API was fed into a barrel section and was transferred forward along the screw length through the other barrel sections towards the exit port where the TDF granules were collected. The barrel temperature profile can be maintained using the temperature control means provided separately to different barrel sections. The temperatures can be as low as about 25° C. and as high as about 60° C. All the barrel sections can also be maintained at the same temperature, if desired. However, the barrel temperatures to be maintained depend on the residence time of TDF in the processor, which in turn depends on the screw speed. These variables can be adjusted to obtain desired quality of TDF granules. The granules can be fed into the twin screw processor by means of specially designed feeders to increase the feed rate.

The twin screw processor enables to prepare a product with even tighter specifications for impurity levels and with an improvement in the compressibility of Tenofovir API.

The twin screw processor enables to prepare a product with minimal increase in impurity levels as compared to the input API. The product so obtained is granular and remains stable even under accelerated stability conditions. The granular compositions of Tenofovir packed in aluminium pouches of 20 micron thickness were found to remain stable.

In accordance with a further embodiment, there is provided a granular Tenofovir composition devoid of an excipient comprising Tenofovir, not more than 1% Tenofovir isoproxil monoester and not more than 0.15% Tenofovir disoproxil dimer.

In accordance with a further embodiment, there is provided a granular Tenofovir composition comprising Tenofovir, not more than 1% Tenofovir isoproxil monoester and not more than 0.15% Tenofovir disoproxil dimer after storage at 40° C. and 75% Relative Humidity for a period of at least 3 months; wherein the composition is devoid of an excipient.

In accordance with a further embodiment, there is provided a granular Tenofovir composition comprising Tenofovir, not more than 1% Tenofovir isoproxil monoester and not more than 0.15% Tenofovir disoproxil dimer after storage at 25° C. and 60% Relative Humidity for a period of at least 3 months; wherein the composition is devoid of an excipient.

In accordance with a further embodiment, there is provided a granular Tenofovir composition comprising Tenofovir, not more than 1% Tenofovir isoproxil monoester and not more than 0.15% Tenofovir disoproxil dimer after storage at 2-8° C. for a period of at least 3 months; wherein the composition is devoid of an excipient.

In accordance with a further embodiment, there is provided a granular Tenofovir composition comprising Tenofovir, not more than 0.15% adenine, not more than 1% Tenofovir isoproxil monoester, not more than 0.15% Tenofovir disoproxil ethylester, not more than 0.3% Tenofovir isopropyl isoproxil, not more than 0.15% Tenofovir disoproxil carbamate, not more than 0.15% Tenofovir disoproxil dimer, not more than 0.10% of any individual unspecified impurity and not more than 2.0% of total impurities; wherein the composition is devoid of an excipient.

In accordance with a further embodiment, there is provided a granular Tenofovir composition comprising Tenofovir, not more than 1% Tenofovir isoproxil monoester and not more than 0.15% Tenofovir disoproxil dimer, prepared by a twin-screw granulation process; wherein the composition is devoid of an excipient.

In accordance with a further embodiment, there is provided a granular Tenofovir composition comprising Tenofovir, not more than 0.15% adenine, not more than 1% Tenofovir isoproxil monoester, not more than 0.15% Tenofovir disoproxil ethyl ester, not more than 0.3% Tenofovir isopropyl isoproxil, not more than 0.15% Tenofovir disoproxil carbamate, not more than 0.15% Tenofovir disoproxil dimer, not more than 0.10% of any individual unspecified impurity and not more than 2.0% of total impurities, prepared by a twin screw granulation process; wherein the composition is devoid of an excipient.

In accordance with the primary embodiment of the present invention, there is provided a process for preparing granular composition of Tenofovir in twin screw processor comprising the steps of
 a. feeding Tenofovir into the intake zone of the twin screw processor;
 b. conveying Tenofovir towards the kneading zone and processing it in the kneading zone;
 c. conveying Tenofovir from the kneading zone towards the exit;
 d. collecting the Tenofovir granules; and wherein the temperature of the barrel is between 25° C. and 60° C., wherein the granules are devoid of an excipient.

In accordance with another embodiment, of the present invention, there is provided a process for preparing tablets comprising Tenofovir, the process comprising the steps of: (a) twin screw granulation of Tenofovir without an excipient to form granules; (b) optionally, sieving the Tenofovir granules; (c) optionally, adding one or more excipients to the mixture; (e) compressing the resulting mixture into tablets.

In accordance with an embodiment of the present invention, the content of Tenofovir in solid oral composition is 200 to 400 mg, more preferably 300 mg. In an embodiment of the present, there is provided a tablet comprising a) the granular composition of Tenofovir prepared in the twin screw processor having content of total impurities of not more than 2.0% and b) one or more pharmaceutically acceptable excipients.

Similarly, the Tenofovir granules can be formulated with other anti-retrovirals or other active pharmaceutical ingredient/s in the form of granules or powders or tablets.

The invention is described by the following non-limiting examples.

EXAMPLES

Example 1

Granules of Tenofovir Disoproxil Fumarate

Tenofovir disoproxil fumarate (TDF) was fed into an OMICRON 10P processor in barrel section B1, STEER ENGINEERING PVT. LTD., Do/Di=1.71 and processed at Screw Speed 300 rpm, Barrel Temperature 25° C. and feed rate of 5.0 g/minute.

The screw configuration was as follows:

TABLE 1

Screw configuration for OMICRON 10P

| | Elements | | | | | | |
|---|---|---|---|---|---|---|---|
| | RSE 10/10 | RSE 20/20 | RSE 10/10 | RKB 45/5/10 | NKB 90/5/10 | RSE 20/20 | RSE 10/10 |
| Number | 1 | 3 | 5 | 2 | 2 | 3 | 2 |

All barrel sections B1/B2/B3/B4 were kept at 25° C. TDF Granules were collected after exiting barrel section B4.

Following were the granule properties:

TABLE 2

Granule properties for TDF granules of Example 1

| Mesh No. | % Cumulative wt. retained |
|---|---|
| #20 (850 μm) | 13.03 |
| #40 (450 μm) | 40.56 |
| #60 (250 μm) | 61.21 |

TABLE 2-continued

Granule properties for TDF granules of Example 1

| Mesh No. | % Cumulative wt. retained |
|---|---|
| #100 (150 μm) | 73.58 |
| Mean Particle Diameter | 350 μm |

Bulk Density (g/cc)—0.542, Tapped Density (g/cc)—0.766, Compressibility Index (%)—29.268, Hausner Ratio—1.414
Analytical Testing
Organic Impurities for Tenofovir Granules The test of organic impurities of Tenofovir Disoproxil Fumarate granules carried out by HPLC (Make-Agilent 1260 Infinity series).

The Tenofovir Disoproxil Fumarate granules sample was analyzed for organic impurities as per method based on Organic impurities, procedure 1 of USP Pending Monographs of Tenofovir Disoproxil Fumarate v.1 Authorized Sep. 1, 2011.

The standard, Tenofovir Disoproxil Fumarate (TDF) was prepared in solution A. concentration 0.502 μg/mL in solution. The sample i.e., TDF granules of the present invention was prepared in solution A, concentration 520.05 μg/mL.

The standard and sample solution was injected in chromatographic system and following impurity results are reported.

TABLE 3

Comparative results of analytical testing for TDF granules of Example 1:

| Impurity | Unprocessed TDF API (%) | Example 1 (%) | Acceptance criteria (%) |
|---|---|---|---|
| Adenine | Not detected | Not detected | NMT 0.15 |
| Tenofovirisoproxil monoester | 0.48 | 0.50 | NMT 1.0 |
| Tenofovirdisoproxil ethyl ester | 0.03 | 0.03 | NMT 0.15 |
| Tenofovir isopropyl isoproxil | 0.17 | 0.18 | NMT 0.30 |
| Tenofovirdisoproxil carbamate | Not detected | Not detected | NMT 0.15 |
| Tenofovirdisoproxil dimer | 0.04 | 0.07 | NMT 0.15 |
| Any individual unspecified impurity | 0.02 | 0.02 | NMT 0.10 |
| Total impurities | 0.84 | 0.90 | NMT 2.0 |

NMT = Not More Than

Observation

From above impurity data, it is apparent that after granulation of TDF, the impurity Tenofovir isoproxil monoester is less than 1.00% and impurity Tenofovir disoproxil dimer is less than 0.15%. Also, the total impurities are less than 1.0%
Preparation of Tablets from Granules of Example 1

The TDF granules of example 1 were compressed using 11 mm standard die punch set.
Quantitative Composition for Unit Dose Tablet

TABLE 4

Quantitative composition for Tenofovir tablet

| Ingredients | Quantity (mg) |
|---|---|
| Tenofovir disoproxil fumarate granules of Example 1 | 300 mg |
| Microcrystalline cellulose | 125 mg |
| Croscarmellose Sodium | 15 mg |
| Magnesium Stearate | 5 mg |
| Fumed silica | 5 mg |
| Total weight | 450 mg |

Tablet Characteristics—
Hardness—7-9 kp, Thickness—5.55 mm, % Friability—0.322, Disintegration time—25-30 seconds Examples 2 to 4: Granules of Tenofovir Disoproxil Fumarate Tenofovir disoproxil fumarate was fed into an OMICRON 10P processor in barrel section B1, STEER ENGINEERING PVT. LTD., Do/Di=1.71 and processed at the following processing conditions

TABLE 5

Processing conditions for Examples 2-4:

| Examples | Screw speed RPM | Feed rate g/min | Barrel temperature profile (° C.) B1/B2/B3/B4 |
|---|---|---|---|
| Example 2 | 300 | 5.0 | 25/40/25/25 |
| Example 3 | 300 | 5.0 | 25/40/40/25 |
| Example 4 | 300 | 5.0 | 25/60/25/25 |

The screw configuration was same as that for Example 1. TDF Granules were collected after exiting barrel section B4.
Tenofovir granules of Examples 2, 3 and 4 were given for analysis: The results are as follows:

TABLE 6

Comparative results of analytical testing for TDF granules of Examples 2-4

| Impurities | Unprocessed TDF API | Example 2 | Example 3 | Example 4 | Acceptance criteria in % |
|---|---|---|---|---|---|
| Adenine | Not detected | Not detected | Not detected | Not detected | NMT 0.15 |
| Tenofovir isoproxil monoester | 0.48 | 0.52 | 0.51 | 0.49 | NMT 1.0 |
| Tenofovir disoproxil ethylester | 0.03 | 0.03 | 0.03 | 0.03 | NMT 0.15 |
| Tenofovir isopropylisoproxyl | 0.17 | 0.17 | 0.17 | 0.17 | NMT 0.30 |

TABLE 6-continued

Comparative results of analytical testing for TDF granules of Examples 2-4

| Impurities | Unprocessed TDF API | Example 2 | Example 3 | Example 4 | Acceptance criteriain % |
|---|---|---|---|---|---|
| Tenofovir disoproxil carbamate | Not detected | Not detected | Not detected | Not detected | NMT 0.15 |
| Tenofovir disoproxil dimer | 0.04 | 0.08 | 0.11 | 0.07 | NMT 0.15 |
| Any individual Unspecified impurity | 0.02 | 0.03 | 0.03 | 0.02 | NMT 0.10 |
| Total impurities | 0.84 | 0.92 | 0.94 | 0.92 | NMT 2.0 |

Example 5

Tenofovir disoproxil fumarate (TDF) was fed into an OMICRON 10P processor in barrel section B1, STEER ENGINEERING PVT. LTD., Do/Di=1.71 and processed at Screw Speed 300 rpm, Barrel Temperature 25° C. and feed rate of 5.0 g/minute. The screw configuration was same as that for Example 1.

All barrel sections B1/B2/B3/B4 were kept at 25° C. TDF Granules were collected after exiting barrel section B4.

Thermal Analysis:

After granulating, the TDF granules were analyzed using DSC. The melting properties obtained from DSC thermogram, were recorded with a DSC instrument (DSC Q200, TA instrument). The DSC Q200 instrument was calibrated for temperature and enthalpy with indium as a certified reference material (m.p.=156.6° C.; Enthalpy of fusion=3.296 (kJ/mol)2. Samples of TDF granules were sealed in standard aluminium pans and heated in the DSC from 25° C. to 250° C., at a heating rate of 5° C./minute. Dry $N_2$ gas, at a flow rate of 50 ml/min, was used to purge the DSC equipment during measurement. The melting point of TDF granules as per example 5 was 117.65° C.

Example 6

Tenofovir disoproxil fumarate was fed into an OMICRON 10P processor, STEER ENGINEERING PVT. LTD., Do/Di=1.71 and processed at Screw Speed 300 rpm, Barrel Temperature 25° C. and feed rate same as Example 1.

The screw configuration was the same as Example 1:

TABLE 7

Screw configuration for OMICRON 10P

| | Elements | | | | | | |
|---|---|---|---|---|---|---|---|
| | RSE 10/10 | RSE 20/20 | RSE 10/10 | RKB 45/5/10 | NKB 90/5/10 | RSE 20/20 | RSE 10/10 |
| Number | 1 | 3 | 5 | 2 | 2 | 3 | 2 |
| Zones | Feeding and metering zone | | | Kneading zone | | Conveying zone | |

All barrels B1/B2/B3/B4 were kept at 25° C. as in Example 1. TDF Granules were collected after exiting barrel section B4.

Following were the granule properties:

TABLE 8

Granule properties for TDF granules of Example 6

| Mesh No. | % Cumulative wt. retained |
|---|---|
| #20 (850 μm) | 10.58 |
| #40 (450 μm) | 38.12 |
| #60 (250 μm) | 56.45 |
| #100 (150 μm) | 70.49 |
| Mean Particle Diameter | 300 |

Bulk Density (g/cc)—0.550, Tapped Density (g/cc)—0.748, Compressibility Index (%)—26.47, Hausner's Ratio—1.36

Stability Testing:

The granules were loaded for stability at the following stability conditions for up to 3 months.

1. 2-8° C.

2. 25° C. and 60% Relative Humidity 3. 40° C. and 75% Relative Humidity

Samples were withdrawn at each month and Impurity testing (for related substances) was performed.

Analytical Testing

Organic Impurities for Tenofovir Granules

The test of organic impurities of Tenofovir Disoproxil Fumarate granules carried out by HPLC (Agilent 1260 Infinity series).

The Tenofovir Disoproxil Fumarate granules sample were analyzed for organic impurities as per Organic impurities, procedure 1 of USP Pending Monographs of Tenofovir Disoproxil Fumarate v.1 Authorized Sep. 1, 2011.

The standard [Tenofovir Disoproxil Fumarate (TDF)] was prepared in solution A. concentration 0.502 μg/mL in solution.

The sample [TDF granules of the present invention] was prepared in solution A, concentration 520.05 μg/mL.

The standard and sample solution was injected in chromatographic system and following impurity results are reported.

TABLE 9

Comparative results of analytical testing for TDF granules of Example 6

| Name of Impurity | Acceptance Criteria (NMT %) USP Pending Monograph API | Acceptance Criteria (NMT %) USP Pending Tablets | Level (%) of the Present Invention Unprocessed (API) initial | Level (%) of the Present Invention Tenofovir DC Grade Granules (Initial) | Stability data (3M) 2-8° C. | Stability data (3M) 25° C./60% RH | Stability data (3M) 40° C./75% RH |
|---|---|---|---|---|---|---|---|
| (R)-9-(2-Phosphonomethoxypropyl)adenine | 0.15 | 0.2 | BDL | BDL | BDL | BDL | BDL |
| Adenine | 0.15 | 0.2 | BDL | BDL | BDL | BDL | BDL |
| Tenofovirisoproxil monoester | 1.0 | 3.0 | 0.321 | 0.355 | 0.420 | 0.555 | 0.766 |
| Tenofovirdisoproxil ethyl ester | 0.15 | — | ND | ND | ND | ND | ND |
| Tenofovir isopropyl isoproxil | 0.3 | — | 0.118 | 0.120 | 0.132 | 0.126 | 0.123 |
| Tenofovir disoproxil Carbamate | 0.25 | — | ND | ND | ND | ND | ND |
| Tenofovirdisoproxil dimer | 0.15 | 0.75 | ND | ND | ND | ND | ND |
| Any individual unknown impurity | 0.1 | 0.2 | 0.015 | 0.036 | 0.055 | 0.068 | 0.263 |
| Total impurity | 2.0 | 4.0 | 0.490 | 0.584 | 0.661 | 0.874 | 1.555 |

List of abbreviations
NMT—Not More Than
BDL—Below Detection Limit
ND—Not Detected
RH—Relative Humidity Observation From above impurity data, it is apparent that after granulation of TDF, the impurity Tenofovir isoproxil monoester is less than 1.00%. Also, the total impurities are less than 2.0%.

It is to be understood that the present invention is susceptible to modifications, changes and adaptation by those skilled in the art. Such modifications changes and adaptations are intended to be within the scope of the present invention.

We claim:

1. A granular composition consisting of Tenofovir, wherein the composition is devoid of an excipient and the content of total impurities is not more than 2.0%, wherein the composition is prepared in a twin screw processor, and wherein the composition is either stable after storage at 40° C. and 75% Relative Humidity for a period of at least 3 months, or the composition is stable after storage at 25° C. and 60% Relative Humidity for a period of at least 3 months, or the composition is stable after storage at 2° C. to 8° C. for a period of at least 3 months.

2. A tablet comprising i) the granular composition of Tenofovir as claimed in claim 1 and ii) one or more pharmaceutically acceptable excipients.

3. The tablet as claimed in claim 2 wherein the pharmaceutically acceptable excipients are microcrystalline cellulose; croscarmellose sodium, magnesium stearate and fumed silica.

4. A process for preparing the granular composition of Tenofovir as claimed in claim 1 comprising the steps of:
   a. feeding Tenofovir into the intake zone of the twin screw processor;
   b. conveying Tenofovir towards the kneading zone and processing it in the kneading zone;
   c. conveying Tenofovir from the kneading zone towards the exit;
   d. collecting the Tenofovir granules; and wherein the temperature of the barrel in the twin screw processor is between 25° C. and 60° C.,
   wherein the granules are devoid of an excipient.

5. The process for preparing granular composition of Tenofovir as claimed in claim 4 wherein the content of Tenofovir isoproxil monoester is not more than 1%; and wherein the content of Tenofovir disoproxil dimer is not more than 0.15%.

6. The process for preparing granular composition of Tenofovir as claimed in claim 4 wherein the content of adenine is not more than 0.15%, the content of Tenofovir isoproxil monoester is not more than 1%, the content of Tenofovir disoproxil ethyl ester is not more than 0.15%, the content of Tenofovir isopropyl isoproxil is not more than 0.3%, the content of Tenofovir disoproxil carbamate is not more than 0.15% and the content of Tenofovir disoproxil dimer is not more than 0.15%.

7. The process for preparing granular composition of Tenofovir as claimed in claim 4 wherein the said composition is stable after storage at 40° C. and 75% Relative Humidity for a period of at least 3 months.

8. The process for preparing granular composition of Tenofovir as claimed in claim 4 wherein the said composition is stable after storage at 25° C. and 60% Relative Humidity for a period of at least 3 months.

9. The process for preparing granular composition of Tenofovir as claimed in claim 4 wherein the said composition is stable after storage at 2° C. to 8° C. for a period of at least 3 months.

* * * * *